United States Patent [19]

Gaydos et al.

[11] 3,962,365

[45] June 8, 1976

[54] PROCESS FOR PRODUCING A MIXTURE OF ISOPROPYLNAPHTHALENES

[75] Inventors: Robert M. Gaydos, Export; Leonard F. Guziak, Monroeville; Robert W. Maxwell, Jr., Pittsburgh, all of Pa.

[73] Assignee: Koppers Company, Inc., Pittsburgh, Pa.

[22] Filed: May 28, 1975

[21] Appl. No.: 581,553

[52] U.S. Cl............................ 260/671 P; 260/671 C
[51] Int. Cl.².......................................... C07C 3/54
[58] Field of Search......... 260/671 P, 671 C, 674 N

[56] References Cited
UNITED STATES PATENTS

| | | | |
|---|---|---|---|
| 2,014,766 | 9/1935 | Isham................................. | 260/671 |
| 2,887,519 | 5/1959 | Hervert.............................. | 260/671 |
| 2,920,121 | 1/1960 | Sisco et al.......................... | 260/674 |
| 2,955,144 | 10/1960 | Sisco et al.......................... | 260/674 |

*Primary Examiner*—Delbert E. Gantz
*Assistant Examiner*—C. E. Spresser
*Attorney, Agent, or Firm*—Oscar B. Brumback; Herbert J. Zeh, Jr.

[57] ABSTRACT

A mixture of monosubstituted and polysubstituted isopropylnaphthalenes is produced by treating naphthalene with concentrated sulfuric acid and propylene. Concentrated sulfuric acid is added to naphthalene in an amount of at least 3% based on the amount of naphthalene used, and at a temperature in the range of 150° – 200°C to form a mixture containing naphthalene sulfonic acids and naphthalene. Propylene is added to this mixture at a temperature of 150° – 220°C. The propylated mixture is neutralized with caustic and distilled to remove naphthalene and to produce a mixture of isopropylnaphthalenes.

2 Claims, No Drawings

PROCESS FOR PRODUCING A MIXTURE OF ISOPROPYLNAPHTHALENES

BACKGROUND OF THE INVENTION

This invention relates to a process for alkylating naphthalene with olefins. More particularly, this invention relates to a process for producing a mixture of isopropylnaphthalenes from naphthalene and propylene in the presence of sulfuric acid.

The alkylation of aromatic compounds with alkylating agents in the presence of sulfuric acid as a catalyst to produce higher molecular weight alkylation products has been known in the art for some time. Alkyl arenes are produced by the alkylation of arenes like benzene, naphthalene, anthracene and other fused-ring aromatic compounds with alkylating agents like olefins, or borate esters or sulfones, or alkyl ethers in the presence of sulfuric acid. If acid strength is sufficient, alkylation and sulfonation occur simultaneously and alkyl aromatic sulfonic acids are produced. The sulfuric acid strength is sufficient when the amount of sulfuric acid is a stoichiometric excess over the amount of aromatic compound. When an olefin is used the ratio of olefin to aromatic compound is at least 2 to 1.

Condensation products of naphthalene are produced by treating the naphthalene with sulfuric acid and olefins. The naphthalene and sulfuric acid react to produce a mixture of alpha and beta naphthalene sulfonic acids. This mixture is caused to react with a mixture obtained by passing propylene and other high molecular weight olefins into concentrated sulfuric acid. The ratio of olefin to naphthalene should be 2 to 1. The temperature must not exceed 100°C. The amount of sulfuric acid is kept at such a high value that it limits the tendency of the olefins to hydrolyze to alchols in the presence of water. The condensation product is purified by being insoluble in water or by precipitation with a strong sulfuric acid. The condensation product may be further purified by treatment with lime and soda which produces the alkali metal salts of the sulfuric acids as the condensation products.

A mixture of monosubstituted and polysubstituted isopropylnaphthalenes is used as a solvent for use in the coatings industry, for use as a low temperature heat transfer solvent, for use as a gasoline and petroleum additive, and for use as a solvent for dyes in chemical microencapsulation processes.

The object of this invention is to provide a process for the production of a mixture of monosubstituted and polysubstituted isopropylnaphthalenes by the use of an insitu prepared catalyst.

SUMMARY OF THE INVENTION

The process of this invention is based on the discovery that naphthalene sulfonic acids act as a catalyst in the reaction of propylene and naphthalene to produce a mixture of mono- and polysubstituted isopropylnaphthalenes. Accordingly, the process of this invention involves:

a. treating naphthalene with at least an amount of three percent of concentrated sulfuric acid at a temperature in the range of 150° to 200°C at atmospheric pressure whereby a mixture containing naphthalene sulfonic acids and naphthalene is produced.

b. adding propylene to the mixture at a temperature in the range of 150°–220°C at atmospheric or superatmospheric pressure to produce an alkylate principally containing monosubstituted and polysubstituted isopropylnaphthalene sulfonic acids and monosubstituted and polysubstituted naphthalenes and some naphthalene.

c. adding caustic to neutralize the alkylate, and d. distilling the alkylate to remove naphthalene and produce an alkylate containing monosubstituted and polysubstituted isopropylnaphthalenes.

The naphthalene sulfonic acids produced in step (a) may be alpha and beta monosulfonic acids along with some polysulfonic acids.

DESCRIPTION OF THE INVENTION

The process of this invention involves four basic steps; catalyst preparation, propylation, catalyst neutralization, and distillation. The process of this invention may be performed in one vessel and the fourth step is performed in another vessel, but the process may also be performed so that each step is conducted in a separate vessel or stage and the reactants cascade from one vessel to the next.

The catalyst preparation step is conducted at a temperature in the range of 150° to 200°C, but preferably in the range of 170°–180°C. At least three parts of concentrated sulfuric acid, based on the weight of naphthalene, are added to 100 parts of naphthalene. Preferably, 3.0 to 6.5 parts of concentrated sulfuric acid (66° Baume) are added to 100 parts of naphthalene. The amount of acid used is 3 to 4% of the naphthalene charged to the reaction vessel. The naphthalene used may have undergone hydrodesulfurization to remove sulfur that might cause noxious odors in the process of this invention. The sulfuric acid reacts quantitatively with naphthalene to form naphthalene sulfonic acids. The sulfonic acids formed consist mostly of alpha and beta naphthalene monosulfonic acids but some polysulfonic acids may be formed. After this acid addition, the temperature is raised preferably to 185°C to drive off all of the water of reaction which is vented to the atmosphere. From this step, a mixture is produced which contains naphthalene and naphthalene sulfonic acids.

In the propylation step propylene is added to the mixture of naphthalene and naphthalene sulfonic acids. The propylene is added at a temperature in the range of 150°–200°C but preferably 180°–200°C. If the temperature is above 220°C, the reaction will be too fast and propylene will be wasted. This would be uneconomical and should be avoided. The amount of propylene added depends on the extent of propylation desired in the final product. The amount of propylene added is varied to meet this desired extent of propylation. The propylation may be conducted at atmospheric pressure throughout the reaction or at a super atmospheric pressure preferably in the range of 5 to 25 psig, for part of the propylation reducing the pressure to atmospheric for the remaining part of the propylation. The propylation also may be conductd entirely at a superatmospheric pressure, if the odor of the final product is of no concern, but if odor is a concern, then the propylation should be conducted to some extent at atmospheric pressure. This operation prevents the formation of noxious compounds. The mixture produced from this step is an alkylate principally containing mono-, and polyisopropylnaphthalene sulfonic acids and mono-, and polysubstituted isopropylnaphthalenes and naphthalene.

This alkylate is neutralized with a caustic. Preferably the alkylate is cooled to a temperature below the boiling point of water. Then a caustic solution is added to the alkylate to neutralize the alkylate to avoid any dealkylation when the alkylate is distilled. Also, the neutralization hinders corrosion of distillation equipment. The caustic may be any alkali metal hydroxide but preferably is a 50% solution of sodium hydroxide. The alkylate is neutralized preferably until the pH is in the range of 7 to 9. Now the alkylate contains mono-, and polysubstituted isopropylnaphthalenes along with naphthalene and salt of the acid.

This neutralized alkylate is distilled to remove naphthalene and to produce the final product of a mixture of mono-, and polysubstituted isopropylnaphthalenes. Preferably the distillation is a fractional distillation at reduced pressure.

According to the provisions of the patent statutes, the principle, preferred construction and mode of operation have been explained and what is considered to represent its best embodiment has been illustrated and described. However, it should be understood that within the scope of the appended claims, the invention may be practiced otherwise than as specifically illustrated and described.

We claim:

1. In a process for producing a mixture of isopropylnaphthalenes wherein naphthalene is reacted with propylene in the presence of a naphthalene sulfonic acid catalyst the Improvement which comprises:
   a. treating naphthalene with concentrated sulfuric acid in an amount of at least 3% based on the amount of naphthalene and at a temperature in the range of 150° to 200°C at atmospheric pressure whereby a mixture containing naphthalene sulfonic acids and naphthalene is produced, and
   b. adding propylene to the mixture at a temperature in the range of 150°–220°C at atmospheric pressure whereby an alkylate is produced containing monosubstituted and polysubstituted isopropylnaphthalenes and naphthalene.

2. A process according to claim 1 wherein the addition of propylene is at a super-atmospheric pressure in the range of 5 to 25 psig.

* * * * *